United States Patent
Heinze et al.

[11] Patent Number: 5,247,945
[45] Date of Patent: Sep. 28, 1993

[54] ELECTRODE ARRANGEMENT FOR A DEFIBRILLATOR

[75] Inventors: Roland Heinze; Karl Stangl, both of Munich, Fed. Rep. of Germany

[73] Assignee: Siemens Aktiengesellschaft, Munich, Fed. Rep. of Germany

[21] Appl. No.: 714,855

[22] Filed: Jun. 13, 1991

[30] Foreign Application Priority Data

Jun. 13, 1990 [DE] Fed. Rep. of Germany ....... 4019002

[51] Int. Cl.⁵ .......................... A61N 1/05; A61N 1/39
[52] U.S. Cl. ........................................ 607/129; 607/6; 607/152
[58] Field of Search .............. 128/642, 784, 785, 798, 128/419 D, 782, 715, 634, 660.03

[56] References Cited

U.S. PATENT DOCUMENTS

| | | |
|---|---|---|
| Re. 27,757 | 3/1987 | Mirowski . |
| 3,805,795 | 4/1974 | Denniston et al. . |
| 3,942,536 | 3/1987 | Mirowski et al. . |
| 4,030,509 | 6/1977 | Heilman et al. . |
| 4,210,149 | 7/1980 | Heilman et al. . |
| 4,291,707 | 9/1981 | Heilman et al. ..................... 128/784 |
| 4,355,642 | 10/1982 | Alferness ............................. 128/642 |
| 4,685,466 | 8/1987 | Rau ................................... 128/642 |
| 4,716,887 | 1/1988 | Kresh et al. . |
| 4,744,952 | 10/1988 | Smits . |
| 4,763,646 | 8/1988 | Lekholm . |
| 4,886,064 | 12/1989 | Strandberg . |
| 4,896,068 | 1/1990 | Nilsson . |
| 4,919,137 | 4/1990 | Schaldach . |
| 4,936,304 | 6/1990 | Kresh et al. . |
| 5,109,842 | 5/1992 | Adinolfi ............................. 128/784 |

FOREIGN PATENT DOCUMENTS

| | | |
|---|---|---|
| 0009255 | 4/1980 | European Pat. Off. . |
| 3523226 | 1/1987 | Fed. Rep. of Germany . |
| 8301582 | 12/1984 | Netherlands ................... 128/419 P |
| 2083363 | 3/1982 | United Kingdom . |

OTHER PUBLICATIONS

"An Optodetector System for Investigating the Contractions of Individual Myocardiocytes," Coch et al., Biomedizinische Technik, vol. 30, No. 7, Aug., 1985, pp. 187-192.

*Primary Examiner*—Lee S. Cohen
*Attorney, Agent, or Firm*—Hill, Steadman & Simpson

[57] ABSTRACT

An electrode arrangement for a cardiac defibrillator includes one or more physiological sensors disposed in an electrode carrier for planar application against the exterior of the heart. The sensor contained in the electrode carrier is connected to a housing, containing a defibrillation power source and signal processing circuitry, via a sensor line, and the electrical signals obtained from the sensor are used for controlling operation of the defibrillator.

12 Claims, 3 Drawing Sheets

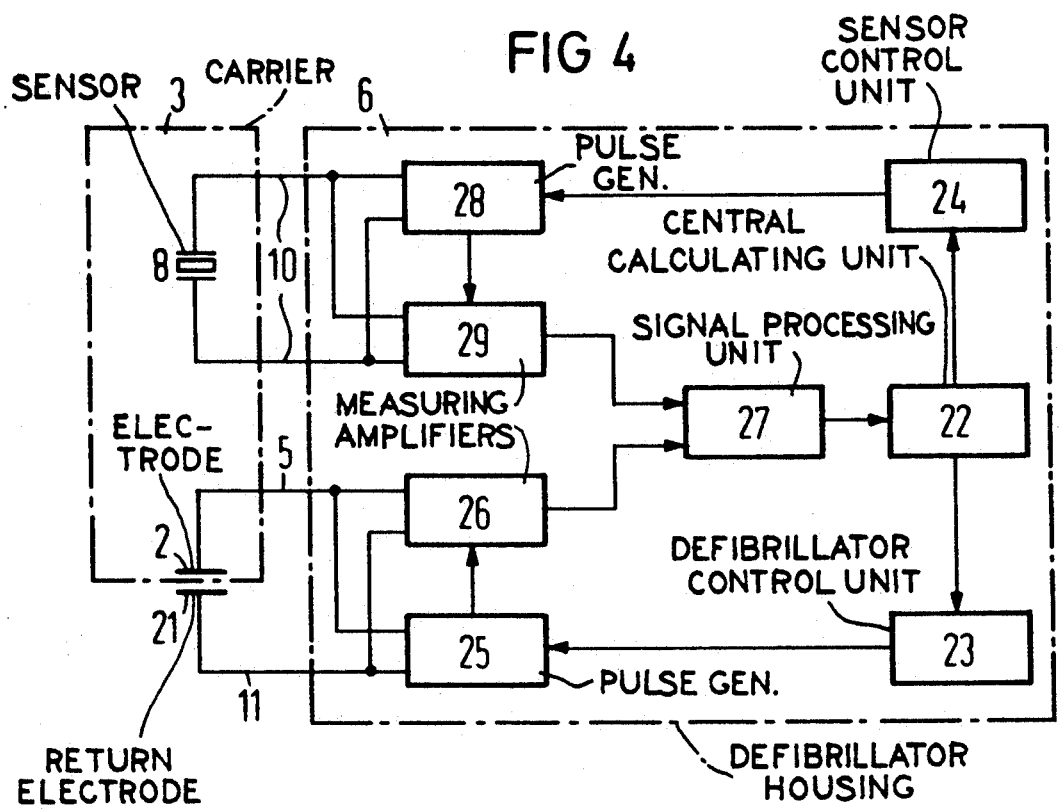
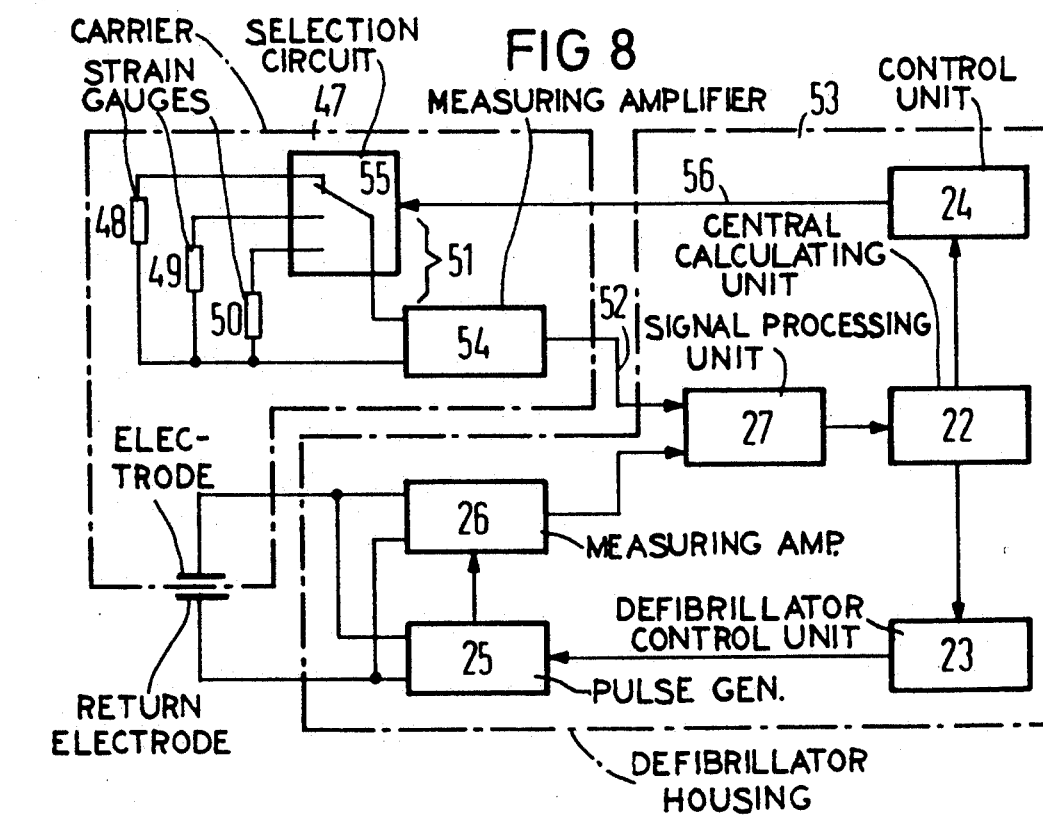

ELECTRODE ARRANGEMENT FOR A DEFIBRILLATOR

BACKGROUND OF THE INVENTION

1. Field of the Invention

The present invention is directed to an implantable cardiac defibrillator, and in particular to an electrode arrangement for such a defibrillator.

2. Description of the Prior Art

Implantable defibrillators are known in the art as disclosed, for example in U.S. Pat. No. 4,030,509 which consists of a defibrillator housing, in which the defibrillation power source and defibrillation processing circuitry are contained, and an electrode connected to the housing via an electrode line for supplying defibrillation therapy, in the form of electrical energy, to the heart. Known electrode arrangements are planar, and are adapted for application against the exterior of the heart so as to be able, insofar as possible, to depolarize all excitable cells of the heart in the event of a cardiac arrhythmia, such as fibrillation, by delivering an output in the form of a current surge from the housing via the electrode line.

In order to initiate and control defibrillation, it is necessary to monitor the functioning of the heart so as to be able to detect, inter alia, tachycardia and/or ventricular flutter. In conventional defibrillators, this is undertaken by intracardial acquisition of selected physiologic parameters in the right side of the heart. In a defibrillator disclosed by European application 0 009 255, for example, a catheter having, inter alia, sensor electrodes is placed in the right side of the heart by which an intracardial ECG is acquired, as well as a signal corresponding to the mechanical pumping action of the heart, obtained indirectly by an impedance measurement.

A cardioverter is disclosed in U.S. Pat. No. 3,942,536 wherein a stimulation catheter is placed in the right side of the heart, which includes a pressure sensor for monitoring the heart function.

A cardioverter is disclosed in U.S. Pat. No. 3,805,795 having a catheter with electrodes for acquiring an ECG and also a sensor for monitoring the muscle contractions of the heart. The sensor consists of an elastic, plastic member having carbon particles embedded therein, the contact resistance of these carbon particles changing upon motion or distortion of the sensor, so that muscle contractions of the heart can be monitored by measuring the overall resistance of the plastic member.

Because the introduction of intracardial sensors can be undertaken without difficulty only in the right side of the heart, no direct monitoring of the functioning of the left side of the heart can be undertaken with such known sensor catheters.

A heart pacemaker having one or more detectors for monitoring heart noises, is disclosed in U.S. Pat. No. 4,763,646, the detectors being in the form of a microphone, a pressure sensor or an acceleration sensor, and the detectors being optionally arranged in an electrode lead of the pacemaker, within the heart pacemaker housing, or outside the heart pacemaker housing connected thereto via a separate lead. This patent discloses placement of the sensors in the proximity of the heart, however, the arrangement of the detectors outside of the heart is not defined so that, for example, a discrimination between heart signals from the right side of the heart and signals from the left side of the heart is not possible without further steps being undertaken, and it is also possible that signals due to other body functions could be superimposed on the signals which are intended to be detected.

SUMMARY OF THE INVENTION

It is an object of the present invention to provide a defined arrangement of one or more sensors relative to the heart in a defibrillation system, without increasing the complexity of the system.

The above object is achieved in accordance with the principles of the present invention, in a defibrillator system, which may be completely implantable, having an electrode arrangement of the type which can be placed in substantially planar fashion (i.e., non-invasive with regard to cardiac tissue) in contact with the exterior of the heart, and having at least one sensor integrated in an electrode carrier of the electrode arrangement, with the sensor being connected to the implantable defibrillator housing via a sensor line for controlling operation of the defibrillator.

The electrode arrangement disclosed herein permits the application of one or more sensors directly at the heart, simultaneously with the application of the defibrillation electrode, so as to permit the functioning of the heart to be monitored. Because the sensor is directly fixed at the heart by means of the defibrillation electrode arrangement, a substantially disturbance-free acquistion of signals corresponding to the functioning of the heart is possible, without these physiologic parameters having to be acquired by a sensor attenuated by intervening muscle or tissue layers in the signal path from the heart to the sensor. Because the sensors are directly fixed at the heart, this also avoids the influence of signals originating with other body functions such as, for example, respiration, being superimposed on the desired signals.

It is also an advantage that the sensor is fixed in a defined position, i.e., a position at the heart which is invariable with respect to the heart geometry. This is particularly useful if signals corresponding to motion of the heart muscle are to be acquired in a reliable manner. The outlay required for applying the sensor in this manner does not exceed the operative outlay already required for applying the defibrillation electrode to the exterior of the heart. In comparison to known, intracardially implanted sensors, the sensor integrated in the electrode carrier is not subject to such a narrow limitation in structural size, so that the use of larger sensors and, thus sensors which are more sensitive and more precise is possible.

The sensor is preferably a microphone, a pressure sensor, an acceleration sensor, a strain sensor or an ultrasound sensor. These types of sensors make the most of the advantage that the sensor is applied directly to the heart, so that motion and noise of the heart can be detected by the sensor unfalsified. Other types of sensors, however, may be used alone or in combination with the aforementioned sensors, such as an optical sensor and/or a measuring electrode for measuring the partial pressure of oxygen, carbon dioxide or other gas concentrations in the tissue of the heart muscle. If an optical sensor is used, it is preferably in the form of a reflection sensor having a light transmitter and light receiver disposed side-by-side, with the portion of light reflected by the tissue of the heart muscle being dependent on the oxygen content of the blood in that tissue. The optical sensor may be placed directly over blood vessels. If an electrode is used for measuring the partial pressure of a gas, the associated passive or return electrode may be formed by the housing of the implanted defibrillator, or may be integrated in the electrode carrier as a ring electrode.

In a preferred embodiment of the invention the electrode carrier has two or more electrode arms or branches, which proceed radially away from a common center, with respective sensors being integrated in at least two of the electrode arms. This makes it possible to place the sensors on the heart at a sufficiently large distance from each other, so that a differential monitoring of the functioning of the heart is possible by forming a difference signal from the individual sensor signals. The same advantage is obtained in a further embodiment of the electrode arrangement wherein the electrode carrier consists of two or more discrete patches, with respective sensors being integrated in at least two electrode patches. This embodiment permits a large area of the heart to the charged by the electrode arrangement, however, since the electrode arrangement does not completely overlie this large area of the heart, heart motions are not detrimentally affected.

In those embodiments wherein a plurality of sensors is integrated in the electrode carrier, a selection circuit can be integrated in the electrode carrier as well so as to avoid a plurality of sensor lines respectively leading between each sensor and the defibrillator housing. The selection circuit connects the outputs of the respective sensors to the processing circuitry in the defibrillator housing one at time, or in selected groups, via a single sensor line dependent on a control signal received from the circuitry in the defibrillator housing.

To enhance the transmission reliability for the cardiac physiologic sensors acquired by the sensors, a measuring amplifier for the sensor or sensors may also be integrated in the electrode carrier.

DESCRIPTION OF THE DRAWINGS

FIG. 4 is a block circuit diagram of the sensor circuitry and the processing circuitry contained in the defibrillator housing, in accordance with the principles of the present invention.

FIG. 8 is a block circuit diagram showing circuitry for use in those embodiments of the invention having a plurality of sensors, including processing circuitry contained in the defibrillator housing.

DESCRIPTION OF THE PREFERRED EMBODIMENTS

Figure 1:
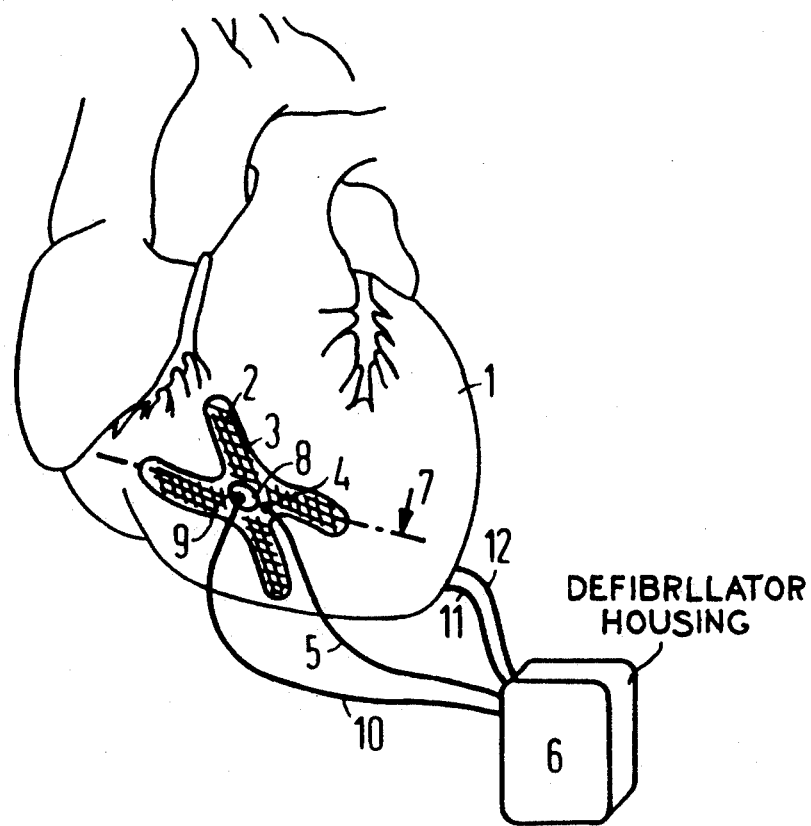
FIG. 1 is a perspective view showing an electrode arrangement of an implantable defibrillator system constructed in accordance with the principles of the present invention, attached to a heart.

A first embodiment of a defibrillator system including an electrode arrangement constructed in accordance with the principles of the present invention is shown in FIG. 1, the electrode arrangement being attached in a known manner to the exterior of a heart 1. The electrode arrangement includes a planar electrode 2 such as a wire mesh electrode, which is contained in a flexible electrode carrier 3. A portion of the electrode 2 is exposed through the carrier 3, and is pressed against the exterior surface of the heart 1. At a terminal location 4, the electrode 2 is electrically connected, via an electrode line 5, to circuitry contained in a defibrillator housing 6, which may be disposed outside of the body of the patient for emergency action or may be implanted in the body of the patient if the patient has a long-term cardiac impairment.

Figure 2:
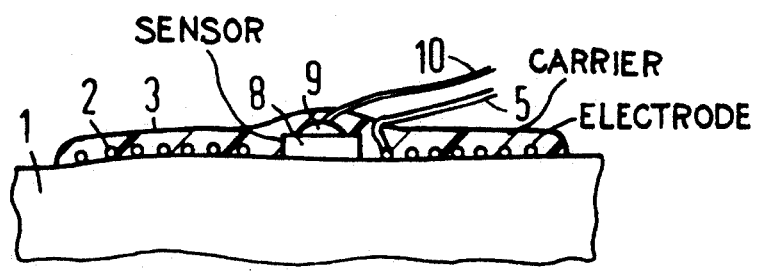
FIG. 2 is a side sectional view of a portion of the electrode carrier shown in FIG. 1.

The electrode carrier 3 consists of a flexible insulating material, preferably silicone rubber, and the electrode 2 is embedded therein in the form of a metal lattice so that the electrode 2, as shown in FIG. 2 (seen along reference line 7 in FIG. 1) lies freely against the outside surface of the heart 1. The electrode 2 is thus exposed at that side of the electrode carrier 3 facing toward the heart 1, and is insulated from the remainder of the body by the electrode carrier 3 at the opposite side.

A sensor 8 is integrated in the flexible electrode carrier 3, which is electrically connected to circuitry in the defibrillator housing 6 at a terminal location 9 via a separate sensor line 10. Although not visible in FIG. 1, a return electrode, also having a sensor, is disposed on the opposite side of the heart 1, facing away from the location at which the electrode 2 is applied. This further electrode and sensor are connected to circuitry in the defibrillator housing 6 via an electrode line 11 and a sensor line 12. The defibrillator housing 6 may contain circuitry, in addition to circuitry for defibrillation and/or cardioversion, pacing the heart with different pacemaker functions, and if so a further intracardially implantable electrode (not shown) will be used.

Figure 3:
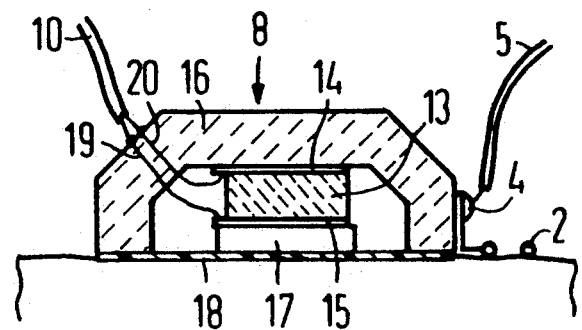
FIG. 3 is a side sectional view showing details of a sensor integrated in the electrode carrier in accordance with the principles of the present invention.

Details of an exemplary embodiment of the sensor 8 are shown in FIG. 3, wherein the sensor 8 is in the form of a piezoelectric measured value sensor which can be selectively used as a microphone, a pressure sensor, an acceleration sensor or an ultrasound sensor. The sensor 8 includes a piezoceramic wafer 13 having two metal layers 14 and 15 at opposite sides serving as electrical contacts, and is arranged in the interior of a pot-like ceramic member 16. The metal layer 14 is glued to an interior base of the ceramic member 16, and the metal layer 15 is connected to a membrane 18 which closes the open side of the ceramic member 16. The metal layer 15 is connected to the membrane 18 via a coupling compound 17, consisting of insulating material. The sensor 8 is embedded in the flexible electrode carrier 3 such that the membrane 18 lies freely exposed at that side of the electrode carrier 3 adapted for application to the heart 1. The ceramic member 16 serves both as a carrier for the terminal location 9, to which the metal layers 14 and 15 are connected via leads 19 and 20 of the sensor line 10, and also serves as carrier for the terminal location 4 at which the electrode 2 is connected to the electrode line 5. The use of the sensor 8 as a microphone, a pressure sensor, an acceleration sensor or an ultrasound sensor is substantially dependent on the respective masses, and the relationships of the masses of the components 16 and 17, as well as on the type of signal processing circuitry used. Once the type of signal evaluation which is desired has been determined, defined, parameter-specific frequency components of the measured signal can be separated from each other by filters, and can be evaluated in parallel as, for example, heart noises (higher-frequency components) or pressure or motion (lower-frequency components).

A block diagram of the sensor 8 in combination with circuitry contained in the defibrillator housing 6 is shown in FIG. 4. As was shown in FIG. 2, the electrode carrier 3 applied to the heart 1 includes the electrode 2 and the sensor 8. A return electrode 21 is allocated to the electrode 2, the return electrode 21 not being shown in FIGS. 1 or 2, but being disposed at that side of the heart 1 facing away from the location at which the electrode 2 is applied, or may be a catheter electrode disposed inside the heart 1. The circuitry contained in the defibrillator housing 6 includes a central calculating unit 22 which controls a defibrillator control unit 23 connected to the electrode 2 and to the return electrode 21, and also controls a sensor control unit 24 connected to the sensor 8. The defibrillator control unit 23, in turn, controls a pulse generator 25, having an output connected via the electrode lines 5 and 11 to the electrode 2 and to the return electrode 21. The pulse generator 25 generates current surges as an output having variable pulse amplitude and pulse duration to the electrodes 2 and 21, under the control of the defibrillation control unit 23. A measuring amplifier 26 is also connected to the electrode 2 and to the return electrode 21, the measuring amplifier 23 permitting, as an option, an ECG measurement or measurement of the heart impedance. The measuring amplifier 26 is disconnected from the electrode 2 for the duration of a current surge output from the pulse generator 25. The output signal of the measuring amplifier 26 is supplied to the calculating unit 22 via a signal processing unit 27 wherein the measured and amplified signals are edited in a known manner, by filtering, for additional processing by the calculating unit 22.

The sensor control unit 23 controls a test pulse generator 28, which enables operation of the sensor 8 connected thereto via the line 10 as an ultrasound generator. A further measuring amplifier 29 measures the heart signals acquired by the sensor 8, and conducts these signals in amplified form to the signal processing unit 27 for additional processing. The calculating unit 22 controls the other circuitry within the defibrillator housing 6 dependent on the measured signals acquired via the electrode 2 and the return electrode 21, as well as based on the signals obtained from the sensor 8. Signals acquired in this manner will exhibit known characteristics, known patters, or a lack of pattern, upon the onset of cardiac arrythmia, and dependent on the sensed signals the circuitry which provides the therapy in the form electrical output signals can be operated in a manner best calculated to treat the specific type of arrythmia which is detected.

Figure 5:
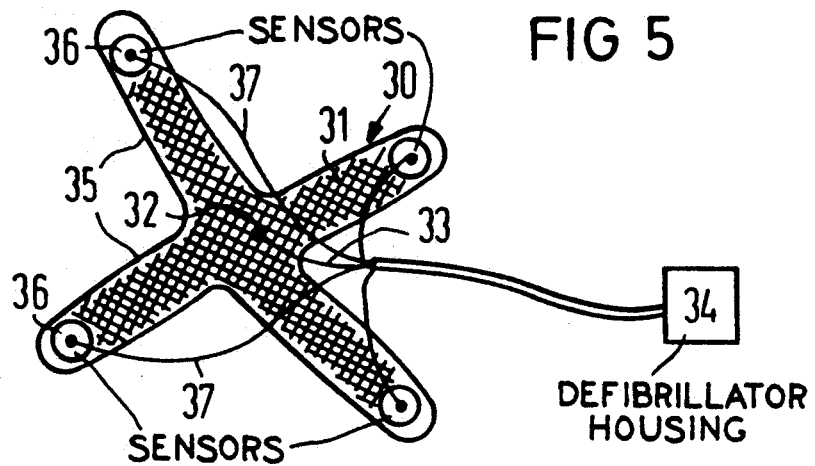
FIGS. 5, 6, and 7 are plan views of respective further embodiments of the electrode arrangement in accordance with the principles of the present invention.

A further embodiment of the electrode arrangement is shown in FIG. 5, having a flexible electrode carrier 30 and a lattice-like electrode 31 embedded therein, connected to a defibrillator 34 at a terminal location 32 via an electrode line 33. In this embodiment, the electrode carrier 30 has a plurality of electrode arms or branches 35, radially diverging from a common central location, and each having an end region in which a respective sensor 36 is integrated. The sensors 36 are each connected to the circuitry in the defibrillator housing 34 via sensor lines 37. The radially extending arrangement of the electrode arms 35 achieves the advantage that the electrode 31 presses against a large area of the heart 1, but does not have the detrimental effect of impeding heart motions. Moreover, the sensors 36 are disposed at relatively large distances from each other, so that the acquisition of signals from different heart regions is possible.

Figure 6:
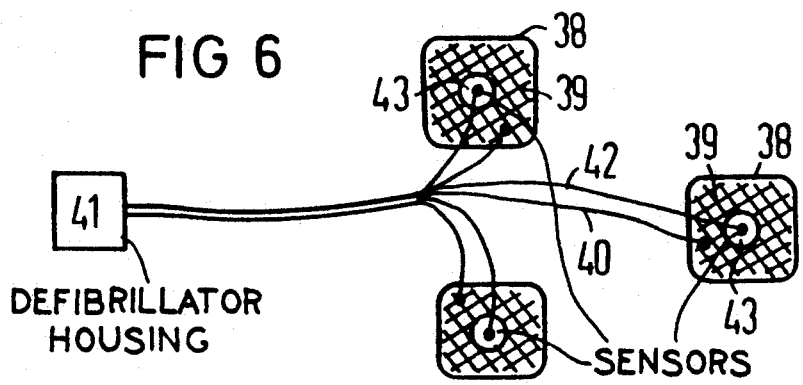

The same advantage is achieved in a further embodiment shown in FIG. 6, wherein the electrode carrier is formed by a plurality of electrode patches 38, having respective electrodes 39 which are individually connected to circuitry in a defibrillator housing 41 via electrode lines 40. Each electrode patch 38 also carries a sensor 43, the sensors 43 being respectively connected to the circuitry in the defibrillator housing 41 via a sensor line 42.

Figure 7:
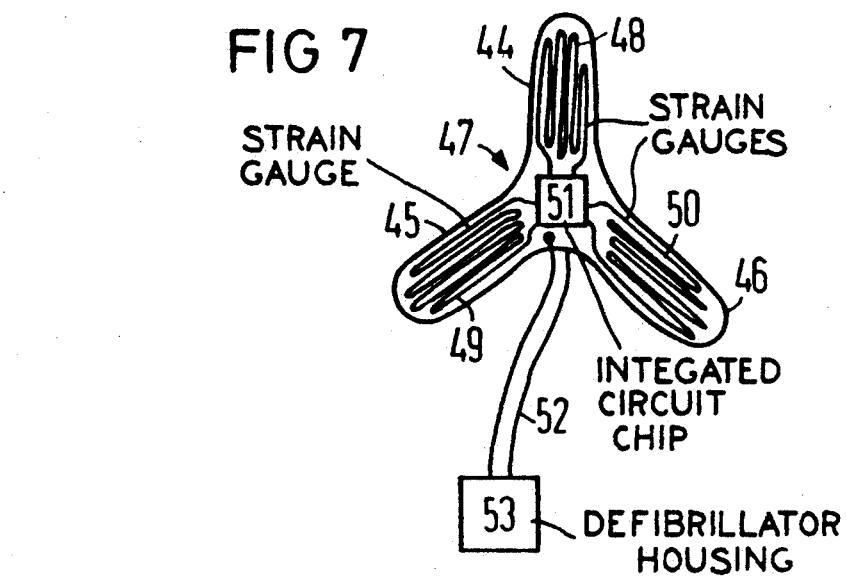

A further embodiment is shown in FIG. 7 wherein strain gauges 48, 49 and 50 are respectively integrated as a sensor in three electrode arms 44, 45 and 46 of an electrode carrier 47. Again, the arms 44, 45 and 46 radially diverge. The strain sensors 48, 49 and 50 are each completely surrounded by the insulating material of the electrode carrier 47, and are insulated from the electrode (not shown in FIG. 7) in the electrode carrier 47. The strain gauges 48, 49 and 50 are connected to a common selection circuit having a measuring amplifier, which is also integrated in the electrode carrier 7 in the form of an integrated circuit chip 51. The strain gauges 48, 49 and 50 are connected to circuitry in the defibrillator housing 53 via a sensor line 52.

A circuit diagram is shown in FIG. 8 for use in embodiments, such as the embodiment of FIG. 7 which have multiple sensors. As already described in connection with FIG. 4, the circuitry in the defibrillator housing 53 includes a calculating unit 22, a defibrillator control unit 23, a sensor control unit 24, a pulse generator 25 and a measuring amplifier 26 connected to the electrode and return electrode. In FIG. 8, the integrated circuit 51 contained in the electrode carrier 47 includes a measuring amplifier 54 having an input side connected to the sensors 48, 49 and 50 via a selection circuit 55. The measuring amplifier 54 has an output side connected to the signal processing unit 27 in the defibrillator housing 53 via the sensor line 52. The selection circuit 53 is connected to the sensor control unit 24 via a control line 56, which is contained in a common insulated housing with the sensor line 52.

Although modifications and changes may be suggested by those skilled in the art, it is the intention of the inventors to embody within the patent warranted hereon all changes and modifications as reasonably and properly come within the scope of their contribution to the art.

We claim as our invention:

1. An electrode arrangement for a defibrillator system comprising:
    an electrode adapted to deliver therapeutic electrical energy to a heart;
    a carrier containing and exposing said electrode at one side of said carrier adapted for placement against the exterior of the heart with said electrode in direct contact with the heart exterior;
    a source for said therapeutic electrical energy;
    an electrode line electrically connecting said electrode to said source of therapeutic electrical energy;
    sensor means for non-invasively measuring a physiologic function related to cardiac activity integrated in said electrode carrier and exposed for direct planar placement against the heart exterior;
    a sensor line connected to said sensor means; and means connected to said sensor line and to said source of therapeutic electrical energy for controlling delivery of said therapeutic electrical energy based on said physiologic function.

2. An electrode arrangement as claimed in claim 1 wherein said sensor means is a microphone.

3. An electrode arrangement as claimed in claim 1 wherein said sensor means is a pressure sensor.

4. An electrode arrangement as claimed in claim 1 wherein said sensor means is an acceleration sensor.

5. An electrode arrangement as claimed in claim 1 wherein said sensor means is an ultrasound sensor.

6. An electrode arrangement as claimed in claim 1 wherein said sensor means is a strain gauge.

7. An electrode arrangement as claimed in claim 1 wherein said sensor means is an optical sensor.

8. An electrode arrangement as claimed in claim 1 wherein said sensor means is a measuring electrode for measuring the partial pressure of gases.

9. An electrode arrangement as claimed in claim 1 wherein said carrier has a plurality of radially diverging electrode arms, wherein said sensor means comprises a plurality of separate sensor elements, and wherein at least two of said electrode arms each have one of said sensor elements integrated therein.

10. An electrode arrangement as claimed in claim 1 wherein said carrier consists of a plurality of separate patches, wherein said sensor means comprises a plurality of separate sensor elements, and wherein at least two of said patches each have one of said sensor elements integrated therein.

11. An electrode arrangement as claimed in claim 1 wherein said sensor means comprises a plurality of sensor elements integrated in said carrier, and further comprising a selection circuit integrated in said carrier connected to each of said sensor elements and to said means for controlling, said selection circuit individually connecting said sensor elements to said means for controlling dependent on a signal received from said means for controlling.

12. An electrode arrangement as claimed in claim 1 wherein said sensor means has a signal output and said electrode arrangement further comprising a measuring amplifier connected to said sensor means signal output and integrated in said carrier.

* * * * *